Feb. 14, 1961 E. S. BOERNER Plant Pat. 2,028
CHRYSANTHEMUM PLANT
Filed May 25, 1960
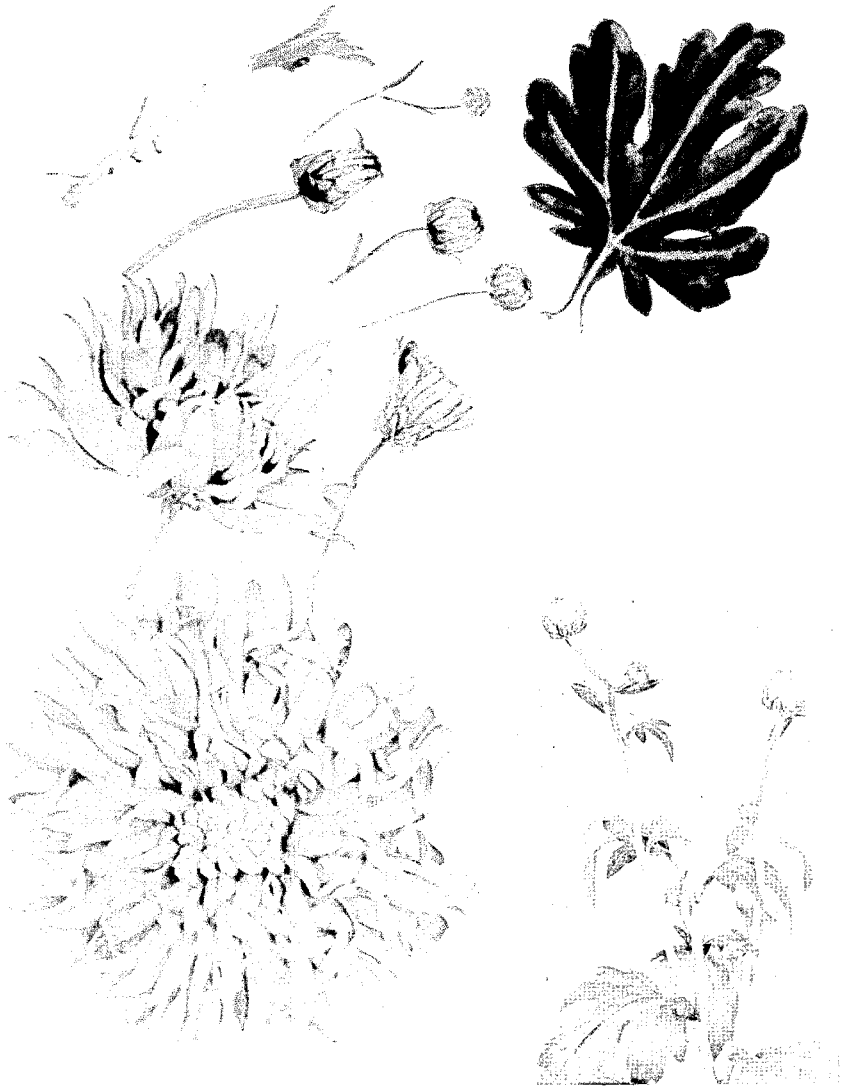
Inventor.
E. S. Boerner
By: Robb & Robb
Attorneys.

United States Patent Office

Plant Pat. 2,028
Patented Feb. 14, 1961

2,028

CHRYSANTHEMUM PLANT

Eugene S. Boerner, Newark, N.Y., assignor to Jackson & Perkins Company, Newark, N.Y., a corporation of New York Filed May 25, 1960, Ser. No. 31,790

1 Claim. (Cl. 47—60)

The present invention relates to a new and distinct variety of chrysanthemum plant of the decorative class, which was originated by me by crossing an unnamed and unpatented seedling derived from a cross of "Meadowlark" (Plant Patent No. 1,305) × "Thrush" (Plant Patent No. 1,168) with the variety "Cockatoo" (Plant Patent No. 1,171).

The primary objective of this breeding was to produce a new chrysanthemum variety having the flower crispness and firmness corresponding to the flowers of "Cockatoo," combined with the hardiness and vigorousness of the unnamed seedling parent. This objective was fully achieved, along with other desirable improvements, as evidenced by the following unique combination of characteristics which are outstanding in the new variety and which distinguish it from its parents as well as from all other varieties of which I am aware:

(1) Hardy and vigorous habits of growth;
(2) Large foliage;
(3) Large flower size, which is unusual for chrysanthemums of this general color;
(4) Crisp and firm flower petals; and
(5) A distinctive Spinel Red color tonality of the flowers.

Asexual reproduction of my new variety by both top cuttings and underground runners, as performed at Newark, New York, shows that the foregoing characteristics and distinctions come true to form and are established and transmitted through succeeding propagations.

The accompanying drawing shows typical specimens of the vegetative growth and flowers of my new variety in different stages of development, and as depicted in color as nearly true as it is reasonably possible to make the same in a color illustration of this character, as well as a typical specimen plant which is depicted in black and white, as illustrative of the form and habit of growth of the plant.

The following is a detailed description of the new variety, with color terminology in accordance with Ridgway's Color Standards and Nomenclature, as based upon observations made from specimens grown outdoors at Newark, New York, in the early afternoon during the latter part of the month of October:

Parentage: Seedling.
*Seed parent.*—An unnamed seedling of "Meadowlark" × "Thrush."
*Pollen parent.*—"Cockatoo."
Classification: Decorative.
Growth: From 2 to 2½ feet tall.
Cold resistance: Very winter hardy in northern New York State; flowers are frost resistant.
Blooming period: In the Newark, New York, climatic area, blooms usually commence in late September and continue to frost.

*Flower*

Bud:
*Color.*—When sepals first divide—Spinel Red, Plate 26. When petals begin to unfurl—Spinel Red, Plate 26, lightly overcast with Rosolane Purple, Plate 26. When half-blown: inside of petals—Spinel Red, Plate 26, lightly overcast with Spinel Pink, Plate 26; outside of petals—Spinel Red, Plate 26.
*Peduncle.* — Color — Absinthe Green, Plate 31. Strength—strong.

Bloom:
*Size.*—5½ inches.
*Stem.*—Stiff; upright.
*Form.*—Decorative.
*Petalage.*—Double.
*Color.*—Center of flower—Spinel Pink, Plate 26, lightly overcast with Spinel Red, Plate 26. Outer petals—Spinel Pink, Plate 26. Base of petals—Clear, Dull Green-Yellow, Plate 17. Inside of petals—Spinel Red, Plate 26. Reverse of petals—Spinel Pink, Plate 26, lightly overcast with Thulite Pink, Plate 26.
*Petals.*—Texture—firm; crisp. Form—oval.
*Fragrance.*—Characteristic chrysanthemum.

*Plant*

Form: Upright; airy.
Growth: Free.
Foliage:
*Size.*—Large.
*Quantity.*—Heavy.
*Color.*—Upper side—Varley's Green, Plate 18. Reverse side—Bice Green, Plate 17.
*Texture.*—Leathery.

I claim:

A new and distinct variety of chrysanthemum plant of the decorative class, substantially as herein shown and described, characterized particularly as to novelty by the unique combination of a hardy and vigorous habit of growth, large foliage, large flower size, crisp and firm flower petals, and a distinctive Spinel Red general color tonality of the flowers.

No references cited.